United States Patent [19]
Horrell, Jr. et al.

[11] Patent Number: 5,262,551
[45] Date of Patent: Nov. 16, 1993

[54] PROCESS FOR ETHYLENE EXPOXIDATION

[75] Inventors: Bennie A. Horrell, Jr.; Stanley B. Cavitt, both of Austin, Tex.

[73] Assignee: Texaco Chemical Company, White Plains, N.Y.

[21] Appl. No.: 34,196

[22] Filed: Mar. 19, 1993

Related U.S. Application Data

[63] Continuation-in-part of Ser. No. 870,979, Apr. 20, 1992, abandoned.

[51] Int. Cl.$^5$ .................. C07D 301/10; C07D 303/04
[52] U.S. Cl. ................................................ 549/534
[58] Field of Search ........................................ 549/554

[56] References Cited
U.S. PATENT DOCUMENTS

| | | | |
|---|---|---|---|
| 2,219,575 | 10/1940 | McNamee et al. | 549/534 |
| 3,957,834 | 5/1976 | Piccinini et al. | 260/348.5 R |
| 3,960,775 | 6/1976 | Piccinini et al. | 252/463 |
| 4,831,162 | 5/1989 | Nakajima et al. | 549/534 |
| 4,904,807 | 2/1990 | Ozero | 549/534 |
| 5,177,225 | 1/1993 | Ramahandran et al. | 549/534 |

FOREIGN PATENT DOCUMENTS

| | | | |
|---|---|---|---|
| 57066 | 8/1982 | European Pat. Off. | 549/534 |
| 1055147 | 1/1967 | United Kingdom | 549/534 |
| 1321095 | 6/1973 | United Kingdom . | |

*Primary Examiner*—Joseph E. Evans
*Attorney, Agent, or Firm*—James L. Bailey; Kenneth R. Priem; Cynthia L. Kendrick

[57] ABSTRACT

Disclosed is an improved process for the epoxidation of ethylene, wherein ethylene is reacted with oxygen in a mol ratio of about one, in the presence of a silver metal catalyst and a halide gas phase inhibitor, at a pressure of about 200 to 300 psig, said improvements comprising: introducing into the reaction zone a feed gas mixture comprising:

30 to 90 mol % ethylene,
0 to 55 mol % methane,
0 to 15 mol % one or more inert, non-hydrocarbon gases or mixtures thereof,
0 to 10 mol % carbon dioxide,
2 to 10 mol % oxygen,
1 to 50 ppm organic halide gas phase inhibitor, and maintaining the temperature in the reaction zone between 180° and 350° C.

14 Claims, 2 Drawing Sheets

PROCESS FOR ETHYLENE EPOXIDATION

This application is a continuation-in-part of application Ser. No. 07/870,979, filed Apr. 20, 1992, now abandoned.

FIELD OF THE INVENTION

This invention relates to the production of ethylene oxide by the epoxidation of ethylene in the presence of a silver-based catalyst. More particularly it relates to an improved process for ethylene epoxidation using a feed gas mixture containing greater than 50 mol % ethylene ballast. The feed gas mixture contains from greater than 50 mol %, or about 51 mol %, to 90 mol % ethylene ballast. When compared with currently used feeds which contain 20 to 30% ethylene, the use of an ethylene ballast allows lower operating temperatures along with slightly higher selectivities, and addresses many of the problems which are known in the art. This invention demonstrates that using ethylene as the ballast gas in ethylene epoxidation is effective, contrary to what is implied by related art; and, it would be a major improvement over the use of methane ballast, which entails considerable initial capital investment in methane purification facilities.

BACKGROUND OF THE INVENTION

It is known in the field of ethylene epoxidation to introduce inert diluents into the reaction zone in order to obtain optimum reaction conditions and/or to avoid the presence of mixtures which are flammable under specific conditions employed. These diluents are called ballast gases or cycle gas diluents. The effectiveness of a number of gases as ballast components has been claimed. Ballast systems disclosed in the past have included methane, ethane, nitrogen, carbon dioxide, and mixtures of two or more of these.

Hydrocarbon ballast gases have a higher heat capacity and thermal conductivity than nitrogen; they facilitate a higher safe oxygen concentration in the cycle gas and assist in moderating the peak reaction temperature. The goal is a higher yield of ethylene oxide at a fixed productivity, or a higher productivity with the same reactor volume and space velocity. Desirable concentrations of ballast gases can be in the range of 30 to 90 mol % of the total feed gas mixture, depending on the explosive limits of the gas mixture employed. Disadvantages to the use of methane or ethane are hydrocarbon purification costs to eliminate sulfur and higher paraffinic hydrocarbons, loss of hydrocarbons through venting of argon and other materials that build up in the process, lower steam generation due to higher heat losses in cycle gas leaving the reactor, and possible safety concerns associated with vapor clouds as a result of rupture-disk failure or equipment damage. Ethane ballast has the additional disadvantage of requiring too much organic halide inhibitor to moderate the reaction; this can cause severe corrosion in the manufacturing unit and pollution problems.

In U.S. Pat. No. 3,119,837 (Jan. 28, 1964) Shell Oil discloses a process wherein methane is used as the ballast gas and is added to the feed to the reaction zone in an amount sufficient to maintain a methane concentration of at least 15 mol %. A related Shell patent is German DE 1,254,137 (Jul. 8, 1968).

In Belgian Patent 707,567 (Jun. 5, 1968) to Halcon International, similar benefits are claimed for the use of an ethane ballast.

U.K. Patent GB 1,382,099 to Halcon (Jan. 29, 1975) discloses processes for ethylene oxidation using various mixed-gas ballasts containing primarily ethane and carbon dioxide. The concentration of ethane is maintained in the range of 10 to 70 vol %. The concentration of carbon dioxide in the reaction mixture is maintained at a level greater than 10% but not more than 70% by volume.

U.K. Patent GB 1,191,983 to Societa Italiana Resine (May 13, 1970) discloses a process for preparing ethylene oxide by catalytic oxidation of ethylene with oxygen in the vapor phase at high temperature (250° to 320° C.) and 1 to 30 atm. pressure. Substantially pure ethylene and oxygen, separately or premixed without gaseous diluents, are introduced into the reactor. The ethylene constitutes more than 86% by volume of the gases entering the reactor. The oxygen comprises only about 4 to 6% of the feed gas. The examples demonstrate only a binary gas mixture; no inert "ballast" is used. Presumably some reaction products would eventually build up in such a system, and change the initial gas concentrations The operating temperatures of U.K. 1,191,983 are 40° to 60° C. above those which will be demonstrated as possible employing the improved process herein disclosed. The improvement in operating temperature, aside from the additional advantages, will indicate the instant invention is a superior process.

E.P. Application 357,292 (Mar. 7, 1990) to ICI suggests that ethylene ballast could be used under a unique set of conditions in which a nitrogen oxide promoter is required. A process is disclosed in which ethylene oxide is produced by contacting a gas stream comprising ethylene and oxygen with a silver-containing catalyst, which is also contacted with a chlorine-containing reaction modifier and an oxide of nitrogen selected from $NO_2$, $N_2O_4$, NO, and $N_2O_3$ by means of the gas stream, which may contain from 35 to 92% by volume of ethylene. In this process, the source of oxygen can be air, oxygen-enriched air, or oxygen from liquid air separation. A distinction between E.P.357,292 and the instant invention is that ICI claims that the nitrate or nitrite forming oxides of nitrogen are necessary to produce certain process improvements; the invention disclosed herein shows that no such oxide of nitrogen is necessary.

To one not skilled in the art, it might seem obvious to use ethylene ballast in ethylene epoxidation. Ethylene has a high heat capacity, which suggests that it could be used with relatively high oxygen concentrations in a fuel-rich system without danger of ignition, provided that the mixture composition is well within the fuel-rich region of the flammability curve. Ethylene should also contribute to increased selectivity. Despite this analysis, there historically have been technical problems which have made ethylene ballasts impractical on a commercial scale. One of the biggest obstacles has been with respect to loss of ethylene by venting of impurities that build up in the cyclic process.

Ethylene epoxidation can be accomplished by means of an air-based or oxygen-based process. In an air-based process, oxidation can be carried out by employing oxygen-nitrogen mixtures, preferably air. In the process, unreacted gases may be recycled to the reactor, but the extent of this recycle is limited by the necessity of removing excess nitrogen, which continuously increases as air is added to the oxidation reactor. When nitrogen is removed, an appreciable portion of the unreacted gases are lost with the nitrogen. In order to limit the loss of ethylene under these conditions, the withdrawn gases are mixed with air and passed through one or more additional oxidation reactors in the presence of the silver catalyst under rather drastic conditions; however, this appreciably increases the manufacturing costs. Another disadvantage is that an unsatisfactory rate of conversion is observed, even though fairly good selectivity can be demonstrated.

In all reactors, as nitrogen is vented, some ethylene is lost through the vent as well. With the reactors employing older processes, including air-based processes, a large amount of nitrogen had to be vented and it was impossible not to lose a large amount of ethylene. Therefore, high concentrations of ethylene in the feed gas mixture were not practically feasible.

In addition, there are major differences in purging between air-based and oxygen-based processes. The air-based process requires a substantial purge stream and a staged reaction-absorption system. With the oxygen-based system, there is a reduction in the amount of inert gases introduced into the closed cycle, resulting in almost complete recycle of the unconverted ethylene. However, carbon dioxide is formed and must be removed on a continuous basis. Process vents are also required to prevent accumulation of argon in the recycle gas. Argon is a major impurity in an oxygen supply derived from cryogenic separation of air components. In spite of this purge, the total vent stream in an oxygen-based process is much smaller than in an air-based unit. The operation of the main reactor in an oxygen-based process can be at much higher ethylene concentration than that possible in an air-based process. The small purge gas flows in an oxygen-based system operated with high-purity oxygen make it more feasible to use fuel-rich ballast systems rather than nitrogen. These diluents facilitate the use of higher oxygen concentrations in the recycle and, therefore, improved selectivity and productivity.

With the more modern reactors or with modifications to the unit gas-venting system, it is now possible to reevaluate what feed gas mixtures could reasonably be used to promote optimal reaction conditions and improve catalyst performance. It is now more practical than in the past to use the cycle gas vents to selectively purge nitrogen and argon through the use of membrane separation, pressure-swing absorption, or a combination of both without losing significant amounts of the most expensive raw material, ethylene.

It would represent a substantial advance in the art if it were possible to use a lower temperature in an ethylene epoxidation process. It would be a distinct commercial advantage if the requirement for methane ballast were reduced. It would represent an advance over the art if no oxides of nitrogen were necessary for such a process to be very effective. With the improved invention described herein, it is now possible to have the aforementioned advantages in a process which provides slightly higher selectivities as well.

SUMMARY OF THE INVENTION

In accordance with the foregoing, the instant invention provides an improved process for the controlled silver-catalyzed oxidation of ethylene by reacting ethylene and oxygen over a modern silver-based catalyst at somewhat lower temperatures than typically employed in the art, in the presence of 2 to 5 ppm halide gas phase inhibitor and employing greater than 50 mol % to 90 mol % ethylene as both a ballast gas and as a reactant. The need for methane, which requires costly purification facilities, is substantially reduced, while essentially providing all the benefits ascribed to methane when used as the principal component of a ballast gas.

DESCRIPTION OF THE PREFERRED EMBODIMENT

Figure 1:
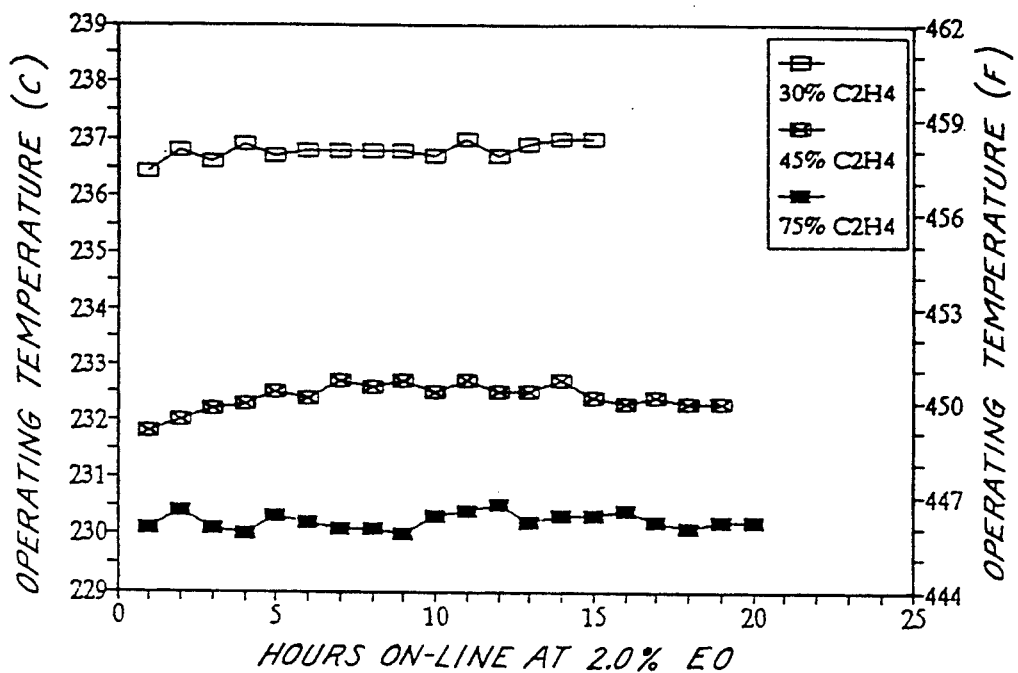
FIG. 1 graphically illustrates the effects of feed ethylene concentration on operating temperature and the effects of feed ethylene concentration on catalyst selectivity.

This invention comprises a process for reacting ethylene and oxygen over a silver-based catalyst and about 2 to 50 ppm halide gas phase inhibitor at a temperature from about 200° to 300° C. and a pressure from about 200 to 300 psig using as a ballast gas about greater than 50 mol % to 90 mol % ethylene.

As discussed above, there are a number of reasons why one of ordinary skill in the art would have previously viewed such a process as impractical. Factors such as, for example, loss of ethylene while venting nitrogen or argon, ethylene polymerization, contamination and other side reactions, as well as safety considerations. The present day, high-quality feed materials, advanced materials of construction, and improved cleaning/passivation procedures would all contribute to the success of this new art as an industrial process. Standard, industrial grade methane and ethylene may be used, preferably with pre-purification using sulfur guard beds that are well-known to those skilled in the art. Oxygen employed as reactant is preferably obtained from air using a suitable separation means, such as cryogenic distillation or pressure-swing absorption processes. The oxygen-containing feed gas suitably has an oxygen concentration of at least 5 mol %, and preferably from about 6 to 10 mol %. Particularly-preferred is a concentration from about 7 to 9 mol %. The amount of oxygen in the oxidation zone of the reactor may vary within the scope of the invention, but must not exceed the flammable limit.

Diluent materials such as, for example, nitrogen, carbon dioxide, argon, methane, etc. may be present in small amounts. Such diluents may be introduced into the system from outside, or may accumulate as a result of reaction processes in the reactor. These materials are normally allowed to recycle until they build up to unwanted proportions, then are vented. Carbon dioxide in particular is removed by absorption into a suitable absorbent material, then discharged from the process by manipulating pressure and/or temperature in a desorber vessel. It is critically important in this process to keep the non-hydrocarbon, non-reacting components at suitably low levels by venting or by absorption/ desorption processes so that the feed gas oxygen concentration is well outside the flammability range, but well inside the fuel-rich region. The amount of carbon dioxide in the reactor feed gas is desirably below about 10 mol %, preferably below about 6 mol %, and most preferably below about 4 mol %. The amounts of argon plus nitrogen are suitably below about 15 mol %, preferably below about 10 mol %, and most preferably below about 6 mol %.

In processes that use molecular oxygen derived from cryogenic separation of air components, small amounts of argon are always present, and these accumulate with time to levels approaching about 15 mol %. It is extremely important in hydrocarbon ballast processes to keep the non-hydrocarbon components at low levels to avoid the presence of flammable mixtures, and to keep the feed oxygen concentration at the highest possible level to attain maximum unit productivity. Nitrogen is no longer an essential component of ethylene oxide ballast gas processes where operation is on the fuel-rich side of the explosive range. High carbon dioxide levels have been shown to be undesirable, in that they lower selectivity and increase the operating temperature required for a fixed ethylene oxide productivity. Carbon dioxide removal technology has improved to such a degree that it is now possible to keep levels at or below 4 mol % in the reactor recycle gas, by using hot carbonate absorbents containing activators to increase efficiency. Liquid-film membranes employing high-capacity amine absorbents, which retard amine entrainment into the cycle gas stream, may be used in conjunction with the instant invention.

The disadvantages to having argon in an ethylene oxide manufacturing process have long been known [U.S. Pat. No. 3,083,213 to Shell Oil Company, Mar. 26, 1963]. It is now technically feasible to selectively remove argon impurities from the more expensive hydrocarbons, such as ethylene and methane, with semipermeable organic or ceramic membranes. Accordingly, the cycle gas vent originally used to purge argon from the system can now be modified with selective membranes to concentrate and purge argon, while retaining a larger proportion of the more expensive hydrocarbons, particularly ethylene. Pressure-swing absorption under cryogenic conditions may also be employed to aid in concentrating and removing argon, while retaining hydrocarbons.

Even though ethylene has a wider flammability range in air than does methane, its possible requirement for a lower inlet oxygen concentration than permitted with methane ballast may be compensated for by adding some ethylene and/or methane directly to the reactor outlet to further reduce the oxygen concentration at that point where a flammable condition is likely to develop. This step will then permit a corresponding increase in oxygen concentration at the reactor inlet.

It is important to note that cleanliness must be maintained in an ethylene ballast system, particularly with respect to iron rust or iron compounds that could cause excessive polymerization or oxidation of ethylene or ethylene oxide.

Catalysts employed in the process of the invention comprise any of the silver metal-containing catalysts disclosed in the art capable of catalyzing the controlled oxidation of ethylene with molecular oxygen to ethylene oxide. These comprise the catalysts consisting essentially of silver metal upon a suitable support. Suitable supports include, for example, any of the siliceous and aluminous support materials. Particularly suitable catalysts are those consisting essentially of silver metal and promoters on low surface area supports containing alpha alumina along with minor proportions of silica, silicon carbide, and other refractory materials. However, the present invention should not be considered limited to the use of any specific silver metal-containing catalyst Halide compounds are used in many ethylene oxide processes as gas phase inhibitors to suppress the undesirable oxidation of ethylene to carbon dioxide and water, although not significantly altering the main reaction to ethylene oxide. The inhibitor is usually an alkyl or alkylene halide, such as ethyl chloride or ethylene dichloride. Other organic halides can be used as well. A considerable amount of inhibitor is required for ethane ballast, and for any ballast process where the ethylene contains a substantial amount of ethane or light paraffinic hydrocarbons other than methane. Ethyl chloride was employed in the instant process. In the instant process, good results were obtained using two to three times the typical amounts of halide required for a methane ballast. A desired concentration was about 2 to 50 ppm, whereas a preferred concentration was about 2 to 20 ppm.

The process of the invention is executed with a relatively high concentration of ethylene ballast in the total charge to the reaction zone. Ethylene may constitute, for example, from about 30 to 90 mol % of the feed to the oxidation zone. A concentration of ethylene in the reactor feed of from 51 mol % to 90 mol % is preferred, and 55 to 85 mol % is particularly preferred. The data in Table III demonstrates, not only good selectivity, but the possibility of obtaining good conversion and selectivity using a lower operating temperature when employing about 60 mol % to 80 mol % ethylene. The examples demonstrate the best selectivity at a lower operating temperature when employing about 75 mol % ethylene. Higher or lower ethylene concentrations may, however, be used within the scope of the invention. Maintaining a specifically desired ethylene concentration is facilitated by controlled addition of some methane as a ballast adjustment, up to about 40 mol % of the gas feed and by control of the amount of materials such as, for example, nitrogen, carbon dioxide, argon, etc. recycled from within the system. In any case a lower mol % of methane would be employed, corresponding to the goal of reducing the necessity of methane purification.

The temperature is suitably in the range of about 150° to 350° C., preferably about 200° to 300° C., and most preferably about 220° to 260° C. The examples demonstrate temperatures between about 215° C. and 240° C. The pressure is suitably in the range from about 100 to 400 psig, and preferably from about 200 to 300 psig. The space velocity is chosen according to how much production is desired, and is preferably in the range of about 2000 to 8000 volumes (or weight) of gas per volume (or weight) of catalyst per hour. These ranges of conditions are those most typically used in current commercial production of ethylene oxide.

In the examples that follow, the use of an ethylene ballast was demonstrated to provide good results and allow efficient catalyst performance in terms of both selectivity and operating temperature. No ethylene polymerization was observed. No abnormal aldehyde level was observed. It did not appear that the high ethylene concentrations resulted in any significant side reactions. The test equipment used in the examples below were tubular, stainless-steel reactors designed to operate with seven grams of catalyst as whole pellets in an isothermal system. The gas mixtures were metered and blended using thermal mass flow controllers. The reactor feed and effluent streams were analyzed using a quadrupole process mass spectrometer. Catalyst selectivities to ethylene oxide were calculated from two averaged selectivities; one based on carbon dioxide and ethylene oxide, and the other on oxygen and ethylene oxide.

It is understood that the following examples are intended only to be illustrative and are not meant to limit the invention in any way.

EXAMPLE 1

Catalyst A was a typical, modern silver-based catalyst for the epoxidation of ethylene. The feed streams consisted of 30–75% ethylene, 8% oxygen, 6% carbon dioxide, 1–3% argon, 2–6 ppm ethyl chloride, and balance methane. The feed flow rate was slightly greater than 300 sccm and reactor pressure was 250 psig. Production of ethylene oxide was kept constant at 2.0% in the effluent stream. The effects of feed ethylene on operating temperature and catalyst selectivity are seen in FIG. 1. As an example, the hourly averaged data points are shown for 75% ethylene in Table I. This data was used in part to calculate overall averages in Table II, which gives an overall average data point for periods shown in FIG. 1. The best results with respect to selectivity and operating temperature were observed using about 75 mol % ethylene (See Table II).

TABLE I

Hourly Averaged Data for Catalyst A

| Hour No. | C2H4 % in | EtCl ppm in | EO % out | Temperature (C.) | Selectivity (%) |
|---|---|---|---|---|---|
| 1 | 73.2 | 5.5 | 2.0 | 230.0 | 80.8 |
| 2 | 73.3 | 5.5 | 2.0 | 230.3 | 80.8 |
| 3 | 73.4 | 5.5 | 2.0 | 230.0 | 80.9 |
| 4 | 73.4 | 5.5 | 2.0 | 229.9 | 80.8 |
| 5 | 74.3 | 5.5 | 2.0 | 230.2 | 80.8 |
| 6 | 74.6 | 5.5 | 2.0 | 230.1 | 80.7 |
| 7 | 74.9 | 5.5 | 2.0 | 230.0 | 80.9 |
| 8 | 75.0 | 5.5 | 2.0 | 230.0 | 80.8 |
| 9 | 75.0 | 5.5 | 2.0 | 229.9 | 80.8 |
| 10 | 74.9 | 5.5 | 2.0 | 230.2 | 80.8 |
| 11 | 74.9 | 5.5 | 2.0 | 230.3 | 80.8 |
| 12 | 74.9 | 5.5 | 2.0 | 230.4 | 80.7 |
| 13 | 74.9 | 5.5 | 2.0 | 230.1 | 80.8 |
| 14 | 74.9 | 5.5 | 2.0 | 230.2 | 80.6 |
| 15 | 74.9 | 5.5 | 2.0 | 230.2 | 80.7 |
| 16 | 74.9 | 5.5 | 2.0 | 230.3 | 80.8 |
| 17 | 74.9 | 5.5 | 2.0 | 230.1 | 80.7 |
| 18 | 74.9 | 5.5 | 2.0 | 230.0 | 80.7 |
| 19 | 74.9 | 5.5 | 2.0 | 230.1 | 80.7 |
| 20 | 74.8 | 5.5 | 2.0 | 230.1 | 80.7 |

TABLE II

Averaged Run Data for Catalyst A

| Hours on-line at 2% EO | Mol % Ethylene in Feed Stream | Average Temperature (C.) | Average % Selectivity | ppm Ethyl Chloride |
|---|---|---|---|---|
| 15 | 30.6 | 236.8 | 79.7 | 2.5 |
| 19 | 45.1 | 232.4 | 80.3 | 3.1 |
| 20 | 74.5 | 230.1 | 80.8 | 5.5 |

EXAMPLE 2

Figure 2:
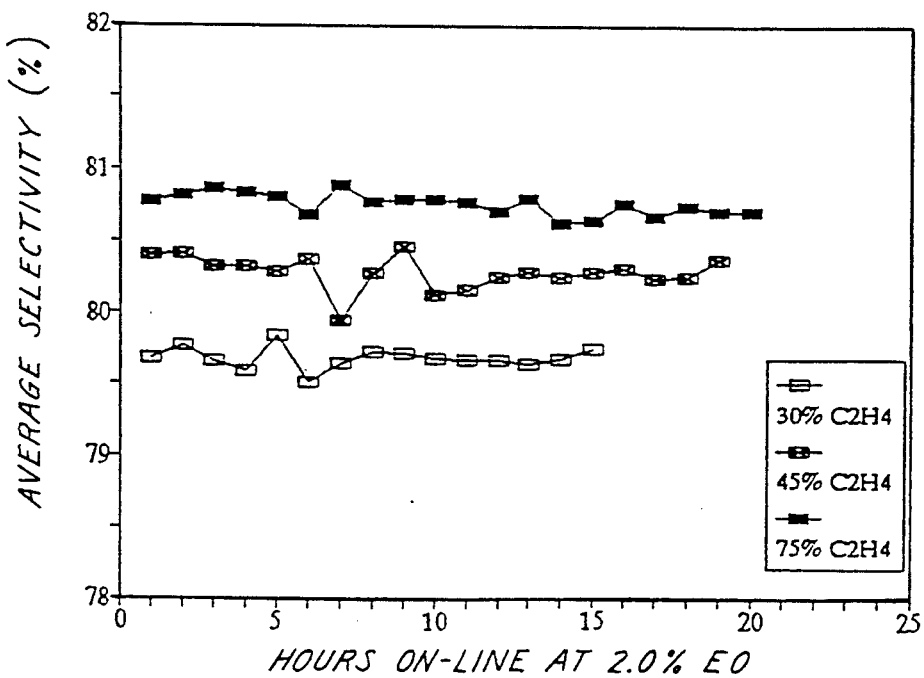
FIG. 2 graphically illustrates the effects of feed ethylene concentration on operating temperature and catalyst selectivity employing the facts of Example 2.
Figure 3:
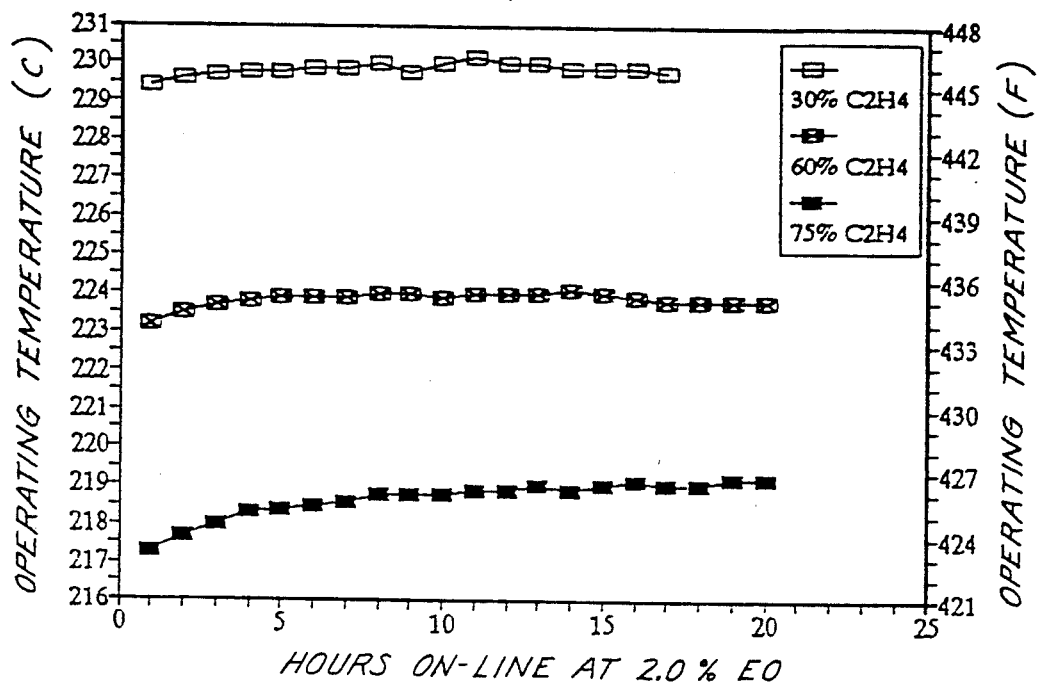
Figure 4:
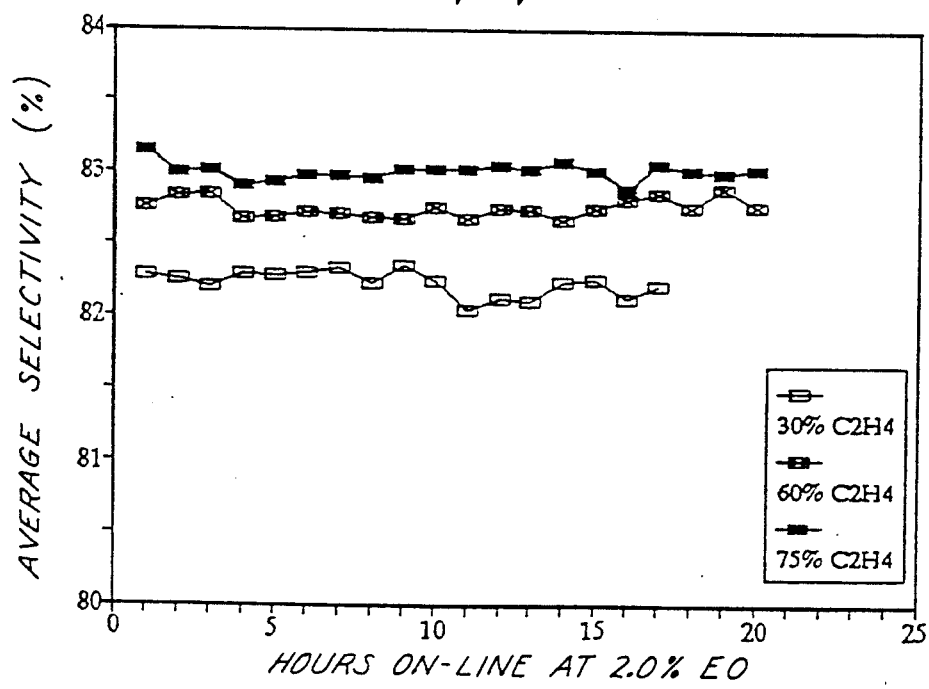

Catalyst B was an experimental, improved silver-based catalyst for the epoxidation of ethylene. The feed streams consisted of 30–75% ethylene, 8% oxygen, 6% carbon dioxide, 1–3% argon, 3–7 ppm ethyl chloride, and balance methane. The feed flow rate was slightly greater than 300 sccm and reactor pressure was 250 psig. Production of ethylene oxide was kept constant at 2.0% in the effluent stream. The effects of feed ethylene on operating temperature and catalyst selectivity are seen in FIG. 2. The data from this graph was used to calculate the overall averages given in Table III. The best results were respect to selectivity and operating temperature were observed using about 60–75 mol % ethylene (See Table III).

TABLE III

Averaged Run Data for Catalyst B

| Hours on-line at 2% EO | Mol % Ethylene in Feed Stream | Average Temperature (C.) | Average % Selectivity | ppm Ethyl Chloride |
|---|---|---|---|---|
| 17 | 30.3 | 229.9 | 82.2 | 4.0 |
| 20 | 60.4 | 223.9 | 82.8 | 3.4 |
| 20 | 74.8 | 218.8 | 83.0 | 6.6 |

SIGNIFICANCE OF RESULTS

An ethylene level of about 30% in the feed represents a typical "methane" ballast operation. When the average selectivities and operating temperatures are compared between a methane ballast containing 30% ethylene, and an ethylene ballast containing 75% ethylene, it is seen from Tables I and II above that the larger ethylene ballast offers slight improvements in selectivity and significant improvements in operating temperature. The increases in selectivities are not altogether unexpected, since more of the reactant was present; however, the significant decreases in operating temperatures, about 7° for Catalyst A and 11° for catalyst B, suggest that use of ethylene ballast, when compared with methane or nitrogen ballasts, could extend the useful lifetime of a catalyst. Also, it should be noted from the above Tables I and II that even levels of 45% and 60% ethylene in the feed result in improved catalyst performance when compared with the typical methane ballast conditions.

What is claimed is:

1. In a process for the production of ethylene oxide wherein ethylene is reacted with oxygen in a mol ratio of ethylene to oxygen of at least about one, in the presence of a silver metal catalyst and halide gas phase inhibitor, at a pressure of about 200 to 300 psig in a reaction zone, the improvements comprising: introducing into the reaction zone a feed gas mixture comprising:
   51 to 90 mol % ethylene,
   0 to 55 mol % methane,
   0 to 15 mol % one or more inert, non-hydrocarbon gases or mixtures thereof,
   0 to 10 mol % carbon dioxide,
   2 to 10 mol % oxygen,
   1 to 50 ppm organic halide gas phase inhibitor, and maintaining the temperature in the reaction zone between 180° and 350° C.

2. The process of claim 1 wherein the pressure in the reactor is between 220 and 275 psig.

3. The process of claim 1 wherein the temperature in the reactor is between 215° and 270° C.

4. The process of claim 1 wherein 51 to 75 mol % ethylene is present in the feed mix.

5. The process of claim 1 wherein no methane is present in the feed gas.

6. The process of claim 1 wherein less than 15 mol %. methane is present in the feed gas.

7. The process of claim 1 wherein 15 to 55 mol % methane is present in the feed gas.

8. The process of claim 1 wherein 0 to 10 mol % argon is present in the feed gas.

9. The process of claim 1 wherein 4 to 8 mol % oxygen is present in the feed gas.

10. The process of claim 1 wherein the halide ga phase inhibitor is ethyl chloride.

11. The process of claim 1 wherein the amount of chloride is between 2 and 25 ppm.

12. The process of claim 1 wherein 2 to 6 mol % carbon dioxide is maintained in the reactor recycle gas.

13. In a process for the production of ethylene oxide wherein ethylene is reacted with oxygen in a mol ratio of ethylene to oxygen of at least about one, in the presence of a silver metal catalyst and halide gas phase inhibitor, at a pressure of about 200 to 300 psig in a reaction zone, the improvements comprising: introducing into the reaction zone a feed gas mixture comprising:
- 51 to 90 mol % ethylene,
- 0 to 55 mol % methane,
- 0 to 15 mol % one or more inert, non-hydrocarbon gases or mixtures thereof,
- 0 to 10 mol % carbon dioxide,
- 2 to 10 mol % oxygen,
- 1 to 50 ppm organic halide gas phase inhibitor, and maintaining the temperature in the reaction zone between 180° and 350° C., and modifying the argon vent to enrich argon in the discharge stream and retain ethylene in the reaction system.

14. In a process for the production of ethylene oxide wherein ethylene is reacted with oxygen in a mol ratio of ethylene to oxygen of at least about one, in the presence of a silver metal catalyst and halide gas phase inhibitor, at a pressure of about 200 to 300 psig in a reaction zone, the improvements comprising: introducing into the reaction zone a feed gas mixture comprising:
- 51 to 90 mol % ethylene,
- 0 to 55 mol % methane,
- 0 to 15 mol % one or more inert, non-hydrocarbon gases or mixtures thereof,
- 0 to 10 mol % carbon dioxide,
- 2 to 10 mol % oxygen,
- 1 to 50 ppm organic halide gas phase inhibitor, and maintaining the temperature in the reaction zone between 180° and 350° C., and adding at the reactor outlet part of the methane and/or ethylene introduced into the feed gas.

* * * * *

UNITED STATES PATENT AND TRADEMARK OFFICE
CERTIFICATE OF CORRECTION

PATENT NO. : 5,262,551
DATED : November 16, 1993
INVENTOR(S) : Bennie Albert Horrell, Jr.
Stanley Bruce Cavitt It is certified that error appears in the above-indentified patent and that said Letters Patent is hereby corrected as shown below:

Column 10,
Claim 10, line 3, after "ga" and insert therefor --s--.

Signed and Sealed this

Twenty-sixth Day of April, 1994

Attest:

BRUCE LEHMAN

Attesting Officer   Commissioner of Patents and Trademarks